United States Patent
Caffey et al.

(10) Patent No.: US 8,467,430 B2
(45) Date of Patent: Jun. 18, 2013

(54) CONTINUOUS WAVELENGTH TUNABLE LASER SOURCE WITH OPTIMUM ORIENTATION OF GRATING AND GAIN MEDIUM

(75) Inventors: David P. Caffey, San Diego, CA (US); Michael Radunsky, Poway, CA (US); Edeline Fotheringham, San Diego, CA (US); Michael Pushkarsky, San Diego, CA (US)

(73) Assignee: Daylight Solutions, Inc., San Diego, CA (US)

( * ) Notice: Subject to any disclaimer, the term of this patent is extended or adjusted under 35 U.S.C. 154(b) by 0 days.

(21) Appl. No.: 13/237,461

(22) Filed: Sep. 20, 2011

(65) Prior Publication Data

US 2012/0076160 A1    Mar. 29, 2012

Related U.S. Application Data

(60) Provisional application No. 61/385,875, filed on Sep. 23, 2010.

(51) Int. Cl.
 *H01S 3/08* (2006.01)
 *H01S 3/10* (2006.01)
(52) U.S. Cl.
 USPC ............... 372/102; 372/20; 372/92; 372/98
(58) Field of Classification Search
 USPC ................. 372/92, 98–99, 102, 20, 101
 See application file for complete search history.

(56) References Cited

U.S. PATENT DOCUMENTS

| 2,684,015 | A | 7/1954 | Grey |
| 3,782,832 | A | 1/1974 | Hacskaylo |
| 4,266,873 | A | 5/1981 | Hacskaylo |
| 4,470,662 | A | 9/1984 | Mumzhiu |
| 4,555,627 | A | 11/1985 | McRae, Jr. |
| 4,656,641 | A | 4/1987 | Scifres et al. |
| 4,737,028 | A | 4/1988 | Smith |

(Continued)

FOREIGN PATENT DOCUMENTS

| DE | 10205310 A1 | 9/2003 |
| EP | 0877 454 A1 | 11/1998 |

(Continued)

OTHER PUBLICATIONS

Weida et al., Utilizing broad gain bandwidth in quantum cascade devices, Nov. 2010, vol. 49 (11) Optical Engineering, 111120, 0091-3286/2010 © 2010 SPIE.

(Continued)

*Primary Examiner* — Kinam Park
(74) *Attorney, Agent, or Firm* — Roeder & Broder LLP

(57) ABSTRACT

An external cavity laser assembly (10) that generates a light beam (12) includes a gain medium (14) and a diffraction grating (24). The gain medium (14) has a growth direction (14C), a fast axis (14A), a first facet (34A), and a second facet (34B) that is spaced apart from the first facet (34A). The gain medium (14) emits from both facets (34A) (34B). Further, a beam polarization (30) of the light beam (32) emitting from the second facet (34B) is perpendicular to the growth direction (14C) and the fast axis (14A). The grating (24) includes a plurality of grating ridges (24A) that are oriented parallel to the beam polarization (30). Moreover, each of the grating ridges (24A) can have a substantially rectangular shaped cross-sectional profile.

20 Claims, 6 Drawing Sheets

U.S. PATENT DOCUMENTS

| | | | |
|---|---|---|---|
| 4,745,276 A | 5/1988 | Broicher et al. | |
| 4,772,789 A | 9/1988 | Maram et al. | |
| 4,796,266 A | 1/1989 | Banwell et al. | |
| 4,852,956 A | 8/1989 | Kramer | |
| 4,871,916 A | 10/1989 | Scott | |
| 4,913,525 A * | 4/1990 | Asakura et al. | 359/559 |
| 5,005,934 A | 4/1991 | Curtiss | |
| 5,050,176 A | 9/1991 | Naito et al. | |
| 5,056,097 A | 10/1991 | Meyers | |
| 5,064,988 A | 11/1991 | E'nama et al. | |
| 5,068,867 A | 11/1991 | Hasenberg et al. | |
| 5,082,339 A | 1/1992 | Linnebach | |
| 5,082,799 A | 1/1992 | Holmstrom et al. | |
| 5,118,186 A | 6/1992 | Schraetzenstaller et al. | |
| 5,140,599 A | 8/1992 | Trutna, Jr. et al. | |
| 5,161,408 A | 11/1992 | McRae et al. | |
| 5,172,390 A | 12/1992 | Mooradian | |
| 5,181,214 A | 1/1993 | Berger et al. | |
| 5,208,417 A | 5/1993 | Langer et al. | |
| 5,225,679 A | 7/1993 | Clarke et al. | |
| 5,255,073 A | 10/1993 | Wallin et al. | |
| 5,264,368 A | 11/1993 | Clarke et al. | |
| 5,315,436 A | 5/1994 | Lowehnar et al. | |
| 5,331,651 A | 7/1994 | Becker et al. | |
| 5,355,609 A | 10/1994 | Schenke | |
| 5,430,293 A | 7/1995 | Sato et al. | |
| 5,457,709 A | 10/1995 | Capasso et al. | |
| 5,476,385 A | 12/1995 | Parikh et al. | |
| 5,491,714 A | 2/1996 | Kitamura | |
| 5,523,569 A | 6/1996 | Hornfeld et al. | |
| 5,537,432 A | 7/1996 | Mehuys et al. | |
| 5,656,813 A | 8/1997 | Moore et al. | |
| 5,662,819 A | 9/1997 | Kadomura | |
| 5,671,561 A | 9/1997 | Johnson et al. | |
| 5,685,636 A | 11/1997 | German | |
| 5,751,830 A | 5/1998 | Hutchinson | |
| 5,752,100 A | 5/1998 | Schrock | |
| 5,780,724 A | 7/1998 | Olender et al. | |
| 5,824,884 A | 10/1998 | Olender et al. | |
| 5,834,632 A | 11/1998 | Olender et al. | |
| 5,854,422 A | 12/1998 | McKeon et al. | |
| 5,862,162 A | 1/1999 | Maeda | |
| 5,866,073 A | 2/1999 | Sausa et al. | |
| 5,892,617 A | 4/1999 | Wallace | |
| 6,089,076 A | 7/2000 | Mueller et al. | |
| 6,134,257 A | 10/2000 | Capasso et al. | |
| 6,154,307 A | 11/2000 | Veronesi et al. | |
| 6,157,033 A | 12/2000 | Chudnovsky | |
| 6,192,064 B1 | 2/2001 | Algots et al. | |
| 6,243,404 B1 | 6/2001 | Joyce | |
| 6,326,646 B1 | 12/2001 | Baillargeon et al. | |
| 6,327,896 B1 | 12/2001 | Veronesi et al. | |
| 6,363,648 B1 | 4/2002 | Kranich et al. | |
| 6,400,744 B1 | 6/2002 | Capasso et al. | |
| 6,431,732 B1 | 8/2002 | Brown et al. | |
| 6,470,036 B1 | 10/2002 | Bailey et al. | |
| 6,483,978 B1 | 11/2002 | Gao et al. | |
| 6,553,045 B2 | 4/2003 | Kaspi | |
| 6,575,641 B2 | 6/2003 | Yamabayashi et al. | |
| 6,578,311 B2 | 6/2003 | Danielson et al. | |
| 6,608,847 B2 | 8/2003 | Wang et al. | |
| 6,616,452 B2 | 9/2003 | Clark et al. | |
| 6,636,539 B2 | 10/2003 | Martinsen | |
| 6,678,429 B2 | 1/2004 | Mossberg et al. | |
| 6,690,472 B2 | 2/2004 | Kulp et al. | |
| 6,714,564 B1 | 3/2004 | Meyers | |
| 6,782,162 B2 | 8/2004 | Fukuzawa et al. | |
| 6,803,577 B2 | 10/2004 | Edner et al. | |
| 6,823,115 B2 | 11/2004 | Greiner et al. | |
| 6,829,417 B2 | 12/2004 | Greiner et al. | |
| 6,856,717 B2 | 2/2005 | Kilian | |
| 6,859,318 B1 | 2/2005 | Mossberg | |
| 6,859,481 B2 | 2/2005 | Zheng | |
| 6,866,089 B2 | 3/2005 | Avila | |
| 6,879,441 B1 | 4/2005 | Mossberg | |
| 6,885,965 B2 | 4/2005 | Butler et al. | |
| 6,909,539 B2 | 6/2005 | Korniski et al. | |
| 6,961,491 B2 | 11/2005 | Greiner et al. | |
| 6,965,464 B2 | 11/2005 | Mossberg | |
| 6,965,716 B2 | 11/2005 | Greiner et al. | |
| 6,985,656 B2 | 1/2006 | Iazikov et al. | |
| 6,987,911 B2 | 1/2006 | Mossberg et al. | |
| 6,990,276 B2 | 1/2006 | Brice et al. | |
| 6,993,223 B2 | 1/2006 | Greiner et al. | |
| 6,995,846 B2 | 2/2006 | Kalayeh et al. | |
| 7,009,743 B2 | 3/2006 | Mossberg | |
| 7,032,431 B2 | 4/2006 | Baum et al. | |
| 7,051,469 B1 | 5/2006 | Pochapsky et al. | |
| 7,054,517 B2 | 5/2006 | Mossberg et al. | |
| 7,061,022 B1 | 6/2006 | Pham et al. | |
| 7,062,128 B2 | 6/2006 | Mossberg | |
| 7,063,260 B2 | 6/2006 | Mossberg et al. | |
| 7,088,076 B2 | 8/2006 | Densham et al. | |
| 7,116,453 B2 | 10/2006 | Mossberg | |
| 7,120,334 B1 | 10/2006 | Greiner et al. | |
| 7,123,794 B2 | 10/2006 | Greiner et al. | |
| 7,151,787 B2 | 12/2006 | Kulp et al. | |
| 7,181,103 B1 | 2/2007 | Greiner et al. | |
| 7,189,970 B2 | 3/2007 | Racca et al. | |
| 7,190,856 B1 | 3/2007 | Iazikov et al. | |
| 7,190,858 B1 | 3/2007 | Greiner et al. | |
| 7,190,859 B2 | 3/2007 | Greiner et al. | |
| 7,194,164 B2 | 3/2007 | Iazikov et al. | |
| 7,203,401 B2 | 4/2007 | Mossberg et al. | |
| 7,224,855 B2 | 5/2007 | Iazikov et al. | |
| 7,224,867 B2 | 5/2007 | Mossberg | |
| 7,231,862 B1 | 6/2007 | Quinn | |
| 7,260,290 B1 | 8/2007 | Greiner et al. | |
| 7,265,842 B2 | 9/2007 | Paldus et al. | |
| 7,286,732 B2 | 10/2007 | Greiner et al. | |
| 7,292,755 B1 | 11/2007 | Greiner et al. | |
| 7,325,318 B2 | 2/2008 | Roes | |
| 7,325,354 B2 | 2/2008 | Grauslys et al. | |
| 7,327,908 B1 | 2/2008 | Iazikov et al. | |
| 7,330,614 B1 | 2/2008 | Mossberg et al. | |
| 7,333,692 B1 | 2/2008 | Mossberg et al. | |
| 7,341,189 B2 | 3/2008 | Mossberg et al. | |
| 7,345,277 B2 | 3/2008 | Zhang | |
| 7,349,599 B1 | 3/2008 | Iazikov et al. | |
| 7,358,498 B2 | 4/2008 | Geng et al. | |
| 7,359,597 B1 | 4/2008 | Iazikov et al. | |
| 7,424,042 B2 | 9/2008 | Day et al. | |
| 7,429,734 B1 | 9/2008 | Tidwell | |
| 7,466,734 B1 | 12/2008 | Day et al. | |
| 7,490,430 B2 | 2/2009 | Staley | |
| 7,492,806 B2 | 2/2009 | Day et al. | |
| 7,505,119 B2 | 3/2009 | Rogers | |
| 7,535,656 B2 | 5/2009 | Day et al. | |
| 7,535,936 B2 | 5/2009 | Day et al. | |
| 7,559,169 B2 | 7/2009 | Hung et al. | |
| 7,590,316 B2 | 9/2009 | Dames | |
| 7,623,234 B2 | 11/2009 | Puzey | |
| 7,732,767 B2 | 6/2010 | Houde-Walter | |
| 7,733,925 B2 | 6/2010 | Pushkarsky et al. | |
| 7,753,549 B2 | 7/2010 | Solinsky et al. | |
| 7,755,041 B2 | 7/2010 | Killinger et al. | |
| 7,796,341 B2 | 9/2010 | Day et al. | |
| 7,818,911 B2 | 10/2010 | Houde-Walter et al. | |
| 7,826,503 B2 | 11/2010 | Day et al. | |
| 7,848,382 B2 | 12/2010 | Weida et al. | |
| 7,873,094 B2 | 1/2011 | Day et al. | |
| 7,920,608 B2 | 4/2011 | Marsland, Jr. et al. | |
| 8,027,094 B2 | 9/2011 | Day et al. | |
| 8,050,307 B2 | 11/2011 | Day et al. | |
| 2002/0024979 A1 | 2/2002 | Vilhelmsson et al. | |
| 2002/0064198 A1 | 5/2002 | Koizumi | |
| 2002/0090013 A1 | 7/2002 | Murry et al. | |
| 2002/0105699 A1 | 8/2002 | Miracky et al. | |
| 2002/0117658 A1 * | 8/2002 | Bandara et al. | 257/14 |
| 2002/0150133 A1 | 10/2002 | Aikiyo et al. | |
| 2002/0176473 A1 | 11/2002 | Mouradian | |
| 2003/0043877 A1 | 3/2003 | Kaspi | |
| 2003/0063633 A1 | 4/2003 | Zhang et al. | |
| 2003/0095346 A1 | 5/2003 | Nasu et al. | |
| 2003/0123495 A1 | 7/2003 | Cox | |
| 2003/0127596 A1 | 7/2003 | Kosterev et al. | |
| 2003/0174315 A1 | 9/2003 | Byren et al. | |

| | | | |
|---|---|---|---|
| 2003/0179789 | A1 | 9/2003 | Pilgrim et al. |
| 2003/0198274 | A1 | 10/2003 | Lucchetti |
| 2004/0013154 | A1 | 1/2004 | Zheng |
| 2004/0032891 | A1 | 2/2004 | Ikeda et al. |
| 2004/0095579 | A1 | 5/2004 | Bisson et al. |
| 2004/0165640 | A1 | 8/2004 | Clifford et al. |
| 2004/0208602 | A1 | 10/2004 | Plante |
| 2004/0228371 | A1 | 11/2004 | Kolodzey et al. |
| 2004/0238811 | A1 | 12/2004 | Nakamura et al. |
| 2004/0264523 | A1 | 12/2004 | Posamentier |
| 2005/0083568 | A1 | 4/2005 | Nakae et al. |
| 2005/0105566 | A1 | 5/2005 | Sacher |
| 2005/0199869 | A1 | 9/2005 | Shi |
| 2005/0213627 | A1 | 9/2005 | Masselink et al. |
| 2005/0237524 | A1 | 10/2005 | Kamei |
| 2006/0056466 | A1 | 3/2006 | Belenky et al. |
| 2006/0088069 | A1* | 4/2006 | Vakhshoori et al. ............ 372/32 |
| 2006/0214107 | A1 | 9/2006 | Mueller |
| 2006/0262316 | A1 | 11/2006 | Baney |
| 2006/0268947 | A1 | 11/2006 | Kalayeh |
| 2007/0019702 | A1 | 1/2007 | Day et al. |
| 2007/0030865 | A1 | 2/2007 | Day et al. |
| 2007/0047599 | A1 | 3/2007 | Wysocki et al. |
| 2007/2029268 | | 9/2007 | Birurakis et al. |
| 2007/0291804 | A1 | 12/2007 | Day et al. |
| 2008/0075153 | A1 | 3/2008 | Roberts et al. |
| 2008/0231719 | A1 | 9/2008 | Benson et al. |
| 2008/0298406 | A1 | 12/2008 | Day et al. |
| 2008/0304524 | A1 | 12/2008 | Marsland et al. |
| 2009/0015914 | A1 | 1/2009 | Duncan et al. |
| 2009/0159798 | A1 | 6/2009 | Weida et al. |
| 2009/0213882 | A1 | 8/2009 | Weida et al. |
| 2009/0257709 | A1 | 10/2009 | Dames |
| 2009/0262768 | A1 | 10/2009 | Day et al. |
| 2010/0002734 | A1* | 1/2010 | Pushkarsky et al. ............ 372/20 |
| 2010/0110198 | A1 | 5/2010 | Larson et al. |
| 2010/0132581 | A1 | 6/2010 | Day et al. |
| 2010/0229448 | A1 | 9/2010 | Houde-Walter et al. |
| 2010/0243891 | A1 | 9/2010 | Day et al. |
| 2010/0291717 | A1* | 11/2010 | Lee-Bouhours ................ 438/31 |
| 2011/0006229 | A1 | 1/2011 | Day et al. |
| 2011/0080311 | A1 | 4/2011 | Pushkarsky et al. |
| 2011/0222566 | A1 | 9/2011 | Weida et al. |
| 2011/0233409 | A1 | 9/2011 | Weida et al. |

FOREIGN PATENT DOCUMENTS

| | | |
|---|---|---|
| EP | 0 883 220 A2 | 12/1998 |
| EP | 2 081 265 A3 | 9/2009 |
| GB | 2286901 A | 8/1995 |
| JP | 55087107 A | 7/1980 |
| JP | 58072108 | 4/1983 |
| JP | 03-048480 A | 3/1991 |
| JP | 07-024322 B | 1/1995 |
| JP | 2005317819 A | 11/2005 |
| WO | W09220127 A1 | 11/1992 |
| WO | WO 03/067720 A2 | 8/2003 |
| WO | WO2008036881 A2 | 3/2008 |
| WO | WO2008036884 A2 | 3/2008 |

OTHER PUBLICATIONS

File:LED, 5mm, green (en).svg—Wikipedia, the free encyclopedia, Description English: A labeled drawing of a 5mm round (the "normal" type) LED. Apr. 6, 2009, 3 pages, http://en.wikipedia.org/wiki/File:LED,_5mm,_green(en).svg.

Sitori, Carlo et al.,"Mid-Infrared (8.5 µm) Semiconductor Lasers Operating at Room Temperature," IEEE Photonics Technology Letters, Mar. 1997, pp. 297-299, vol. 9, No. 3, XP000684396, ISN:1041-1135, © 1997 IEE.

W.Y. Oh et al, "115 kHz tuning repetition rate ultrahigh-speed wavelength-swept semiconductor laser", received Apr. 11, 2005, accepted Aug. 9, 2005, pp. 3159-3163, vol. 30, No. 23, Optics Letters, © 2005 Optical Society of America.

Weida et al., "Tunable QC laser opens up mid-IR sensing applications," Jul. 2006, pp. 1-5, Laser Focus World, http://www.optoiq.com/index/photonics-technologies-applications/lfw-display/lfw-articles-tools-teplate/_pr.

G. Totschig et al.,Mid-infrared external-cavity quantum-cascade laser XP-001161786, Oct. 15, 2002, pp. 1788-1790, Optics Letters/vol. 27, No. 20, © 2002 Optical Society of America.

Thierry Aellen et al., Continuous-wave distributed-feedback quantum-cascade lasers on a Peltier cooler, Sep. 8, 2003, pp. 1929-1931, Applied Physics Letters, vol. 83, No. 10, © 2003 American Institute of Physics.

Cassidy et al., Short-external-cavity module for enhanced single-mode tuning of InGaAsP and AlGaAs semiconductor diode lasers, Oct. 1991, No. 10, pp. 2385-2388, © 1991 American Institute of Physics.

M.G. Littman, H.J. Metcalf: "Spectrally narrow pulse dye laser without beam expander" Applied Optics, vol. 17, No. 14, Jul. 15, 1978, pp. 2224-2227, XP002528173 US.

Patrick McNicholl and Harold J. Metcalf, Synchronous cavity mode and feedback wavelength scanning in dye laser oscillators with gratings, Sep. 1, 1985, pp. 2757-2761, vol. 24, No. 17, Applied Optics, © 1985 Optical Society of America.

Victor Rudometov and Eugene Rudometrov, Peltier Coolers, May 11, 2005, pp. 1-11, http://www.digit-life.com /article/peltiercoolers.com/ © Digit-Life.com 1997-2004.

T Topfer, KP Petrov, Y Mine, D Jundt, RF Curl, and FK Tittel, Room-temperature mid-infrared laser sensor for trace gas detection, Applied Optics, Oct. 20, 1997, pp. 8042-8049, vol. 36 No. 30, Oct. 20, 1997/Applied Optics.

Cavity Enhancing Sensors using QC Lasers, Jun. 7, 2005, pp. 1-6, http://www.infrared.phl.gov/enhanced.sensors.html, Webmaster: Pamela Kinsey, Reviewed: Nov. 23, 2004.

Transient FM Absorption Spectroscopy, Jun. 7, 2005, pp. 1 and 2, http://www.chem/tamu.edu/group/north/FM.html.

FM Spectoscopy With Tunable Diode Lasers, Application Note 7, pp. 1-10, New Focus Copyright 2001.

John Andrews and Paul Dalin,Frequency Modulation Spectroscopy, Dec. 2005, pp. 24-26, http://www.spectroscopyeurope.com.

R.F. Curl and F.K. Tittel,Tunable infrared laser spectroscopy, 1998, pp. 219-272, Annu. Rep. Prog-Chem. Sect. C, 2002.

Shawn Wehe et al., AIAA 2002-0824 Measurements of Trace Pollutants in Combustion Flows Using Room-Temperature, Mid-IR Quantum Cascade Lasers , S. Wehe, et al. (Physical Sciences, Inc.) C Gmachi and F Capasso (Bell Lab., Lucent Technologies), Jan. 2002, cover and pp. 1-7, 40th AIAA Aerospace Sciences Meeting and Exhibit 14, Jan. 17, 2002, Reno, NV.

W. Huang, RRA Syms, J. Stagg and A.A. Lohmann, Precision MEMS Flexure mount for a Littman tunable external cavity laser, Mar. 2004, pp. 67-75, IEE Prc-Sci Meas. Technol vol. 151, No. 2 Mar. 2004.

K. Namjou, S. Cai, E.A. Whitaker, J. Faist, C. Gmacahi, F. Capasso, D.L. Sivco and A.Y. Cho,Sensitive absorption spectroscopy with a room-temperature distributed-feedback quantum-cascade laser, 1998, pp. 219-221, 1998 Optical Society of America.

Gregory E. Hall and Simon W. North,Transient Laser Frequency Modulation Spectroscopy, 2000, pp. 243-274, Annu. Rev.Phys. Chem. 2000.51:243-74-Copyright 2000.

External-cavity quantum-cascade lasers, May 11, 2005, pp. 1-4, http://www.unine.ch/phys/meso/EC/EC.html.

Frequency stabilization of diode lasers, May 30, 2005, pp. 1-17, Santa Chawla—National Physical Laboratory, http://www.ias.ac.in/currsci/jan25/articles4l.htm, National Physical Lab, New Delhi 110 012 India.

R.A. Syms, A. Lohmann, MOEMS Tuning Element for a Littrow External Cavity Laser, Dec. 2003, pp. 921-928, Journal of Microelectromechanical Systems, vol. 12, No. 6 Dec. 2003.

A.A. Koserev et al., Thermoelectrically cooled quantum cascade laser based sensor for continuous monitoring of ambient atmospheric CO—AA Koserev, FK Tittel, R Kohler, C Gmachi, F Capasso, DL Sivco, AY Cho, S Wehe and M Allen, 2002, cover and pp. 1-16, Copyright 2002 Optical Society of America (provided in parent U.S. Appl. No. 11/154,264).

Cooke, M., Producing more light than heat from quantum cascade lasers, published on-line Jan. 10, 2010, www.semiconductor-today.com, Semiconductor Today, vol. 5, Issue 1, pp. 106-107, Feb. 2010.

Lincoln Laboratory, News, MIT Lincoln Laboratory creates bright diode lasers, posted on-line Oct. 2009, pp. 1-2, MIT Lincoln Laboratory:News: MIT Lincoln Laboratory creates bright diode lasers, © 2011 Lincoln Laboratory, Massachusetts Institute of Technology.

Lincoln Laboratory, Publications, Lab Notes, Laser Technology, A Bright Idea, Simple tweaks turn into tiny diode lasers into powerhouses, posted on-line Jun. 2010, pp. 1-3, MIT Lincoln Laboratory:Lab Note: A Bright Idea, © 2011 Lincoln Laboratory, Massachusetts Institute of Technology.

Michael Hacskaylo, "Laser Aiming Light," Army Electronics Command Fort Belvoir, VA Night Vision Lab, Jan. 1974, 26 pages, US Department of Commerce, Technology Administration, National Technical Information Service, Springfield, VA 22161.

Lawrence T. Marshall et al., "Integrated Sight,"CECOM RDEC Night Vision and Electronic Sensors Directorate, Fort Belvoir, VA, Texas Instruments, Inc., Plano, TX, Jun. 1997, 8 pages, SPIE vol. 3080, 0277-786X/97, SPIE Digital Library.

T.L. Myers et al., "FY 2005 Quantum Cascade Laser Alignment System Final Report," Dec. 2005, 52 pages, PNNL-15600, Pacific Northwest National Laboratory, prepared for the U.S. Department of Energy.

Joe S. Randella et al., "The Integrated Sight: Future Improvement for Land Warrior,"Aug. 1998, pp. 62-72, Proceedings of the SPIE—SPIE vol. 3394, The International Society for Optical Engineering, SPIE Digital Library.

Jacob B. Khurgin et al., "Transport and gain in a quantum cascade laser model and equivalent circuit," Nov. 2010, 9 pages, Optical Engineering 49(11), 111110, SPIE Nov. 2010/vol. 49 (11), © 2010 SPIE, SPIE Digital Library.

Shunt Switched Current Control. Applicant admits that this circuit design is prior art and used more than one year prior to Aug. 16, 2010.

QC Current Regulator. Applicant admits that this circuit design is prior art and used more than one year prior to Aug. 16, 2010.

Thorlabs, Thorlabs.com—Tunable Lasers:Littrow and Littman Prealigned Kits, OFC Information Sheet 2011, http://www.thorlabs.us/newgrouppage9.cfm?objectgroup_id=4757, © 1999-2011 Thorlabs.

Oleksiy Andrusyak et al., External and common-cavity high spectral density beam combining of high power fiber lasers, Jan. 1, 2008, Proc. of SPIE vol. 6873, SPIE Digital Library.

Thomas Schreiber et al., Incoherent Beam Combining of Continuous-Wave and Pulsed Yb-Doped Fiber Amplifiers, Mar. 1, 2009, vol. 15, No. 2, © 2009 IEEE.

Hildebrandt, L.et al.."Quantum cascade external cavity laser systems in the mid-infrared spectral range," 2004, Sacher Lasertechnik Group, Marburg, Germany.

Haim Lotem, Mode-hop suppression of Littrow grating-tuned lasers: comment, 20 Month 1994, p. 1, vol. 33, No. 00, Applied Optics.

Corrie David Farmer, "Fab and Eval. Of QCL's", Sep. 2000, Faculty of Engineering, University of Glasgow, Glasgow, UK.

M. De Labachelerie and G. Passedat, Mode-hop suppression of Littrow grating-tuned lasers, Jan. 20, 1993, pp. 269-274, vol. 32, No. 3, Applied Optics, © 1993 Optical Society of America.

S. Blaser et al., Alpes Lasers, Room-temperature continuous-wave single-mode quantum cascade lasers, Photonics West 2006, Novel In-Plane Semiconductors V:Quantum Cascade Lasers:6133-01 Switzerland.

Gaetano Scamarcio, Mid-IR and THz Quantum Cascade Lasers, 2005, Physics Dept., University of Bari, Bari Italy.

Gaetano Scamarcio et al., Micro-probe characterization of QCLs correlation with optical performance, APL 78, 1177 & APL 78, 2095 (2001), APL 2002, APL 2004, University of Bari, Bari Italy.

J. Faist, THz and Mid-IR Quantum cascade lasers, QM in space, Chatillon, Mar. 31, Science 2002, University of Neuchatel, EU Projects Answer/Teranova; Agilent, Funding Swiss National Science Foundation.

Joel M. Hensley, Recent Updates in QCL-based Sensing Applications, Sep. 5-10, 2006, Physical Sciences, Inc., Andover, MA, 2nd International Workshop on Quantum Cascade Lasers, Ostuni, Italy.

J.M. Hensley et al., Demonstration of an External Cavity Terahertz Quantum Cascade Laser, Copyright 2005, Optical Society of America, Washington, DC 20036.

L. Hildebrandt et al., Quantum cascade external cavity and DFB laser systems in the mid-infrared spectral range: devices and applications, 2004, Marburg Germany.

Richard Maulini et al., Broadly tunable external cavity quantum-cascade lasers, 2005, University of Neuchatel, Neuchatel Switzerland.

Tsekoun, A. et al; "Improved performance of QCL's through a scalable, manufacturable epitaxial-side-down mounting process"; Feb. 2006.

Pushkarsky, M. et al.; "Sub-parts-per-billion level detection of NO2 using room temp. QCLs"; May 2006.

Wirtz, D. et al.; "A tuneable heterodyne infrared spectrometer"; Physikalisches Institut; University of Koln; Koln Germany Spectrochimica 2002.

Williams, B. et al.;"Terahertz QCLs and Electronics"; PhD-MIT 2003.

PCT/US2011/028780 filed Mar. 17, 2011, Daylight Solutions, Inc. PCT International Application No. PCT/US2011/028780 and its entire prosecution history.

PCT/US2011/43065 filed Jul. 6, 2011, Daylight Solutions, Inc. PCT International Application No. PCT/US2011/443065 and its entire prosecution history.

U.S. Appl. No. 13/177,332, filed Jul. 6, 2011, Daylight Solutions, Inc. U.S. Appl. No. 13/177,332, filed Jul. 6, 2011 and its entire prosecution history.

U.S. Appl. No. 13/211,186, filed Aug. 16, 2011, Daylight Solutions, Inc. U.S. Appl. No. 13/211,186, filed Aug. 16, 2011 and its entire prosecution history.

U.S. Appl. No. 13/221,721, filed Aug. 30, 2011, Daylight Solutions, Inc. U.S. Appl. No. 13/221,721, filed Aug. 30, 2011 and its entire prosecution history.

U.S. Appl. No. 13/267,787, filed Oct. 6, 2011, Daylight Solutions, Inc. U.S. Appl. No. 13/267,787, filed Oct. 6, 2011 and its entire prosecution history.

U.S. Appl. No. 13/303,088, filed Nov. 22, 2011, Daylight Solutions, Inc. U.S. Appl. No. 13/303,088, filed Nov. 22, 2011 and its entire prosecution history.

Martini, Rainer, et al., "High duty cycle operation of quantum cascade lasers based on graded superlattice active regions", Journal of Applied Physics, Jun. 15, 2001, pp. 7735-7738, vol. 89, No. 12, XP012052642 ISSN:0021-8879, © 2001 American Institute of Physics.

Luo, G.P., et al., "Grating-tuned external-cavity quantum-cascade semiconductor lasers", May 7, 20011, Applied Physics Letters, vol. 78, No. 19, © 2001 American Institute of Physics.

Wysocki, G., et al., "Widely tunable mode-hop free external cavity quantum cascade laser for high resolution spectroscopic applications", Jul. 27, 2005, Applied Physics, B81, pp. 769-777, Applied Physics B Lasers and Optics.

Day, Timothy, et al., "Miniaturized External Cavity Quantum Cascade Lasers for Broad Tunability in the Mid-Infrared", May 21, 2006, 1-55752-813-6, Lasers and Electro-Optics and 2006 Quantum Electronics and Laser Science Conference © 2006 IEEE.

Weidmann, D., et al., "Development of a compact quantum cascade laser spectrometer for field measurements of CO2 isotopes", Feb. 1, 2005, pp. 255-260, Applied Phys. B 80, Applied Physics B Lasers and Optics, Published online Sep. 29, 2004, © 2004 Springer-Verlag.

US 7,733,928, 06/2010, Marsland, Jr. et al. (withdrawn)

* cited by examiner

CONTINUOUS WAVELENGTH TUNABLE LASER SOURCE WITH OPTIMUM ORIENTATION OF GRATING AND GAIN MEDIUM

RELATED APPLICATION

This application claims priority on U.S. Application No. 61/385,875, filed on Sep. 23, 2010, and entitled "Continuous Wavelength Tunable Laser Source With Optimum Orientation Of Grating And Gain medium". As far as permitted, the contents of U.S. Application No. 61/385,875 are incorporated herein by reference.

BACKGROUND

Lasers are commonly used to generate light. One type of laser includes a wave guided gain medium, collimating optics (collimator), and a plane diffraction grating, retroreflacting light, which together define an external cavity for the laser. This type of laser is commonly referred to as having a Littrow configuration. In this configuration, light generated by the gain medium is directed through the collimator at the diffraction grating, and the diffraction grating reflects the light back to the gain medium through the collimator. With this design, the primary wavelength of the light generated by the laser is dependent upon the angle of incidence of the collimated light on the diffraction grating.

In certain designs, it is desirable that the laser can be selectively and continuously tuned across a desired wavelength (or frequency) range. With a Littrow type laser, the output wavelength can be adjusted continuously by simultaneous adjustment of (i) the grating angle with respect to the incident beam, and (ii) the cavity length of the external cavity.

SUMMARY

The present invention is directed to an external cavity laser assembly that generates a light beam. In one embodiment, the laser assembly includes a gain medium and a diffraction grating. The gain medium has a growth direction, a fast axis, a first facet, and a second facet that is spaced apart from the first facet. The gain medium generates the light beam when electrical current is directed through the gain medium, and the gain medium emits from both facets. Further, a beam polarization of the light beam emitting from the second facet is perpendicular to the growth direction and the fast axis. The diffraction grating is positioned in the path of the laser beam that emits from the second facet, and reflects at least a portion of the incident light. Further, as provided herein, the grating includes a plurality of grating ridges that are oriented substantially parallel to the beam polarization, and substantially perpendicular to the fast axis of the gain medium.

With this design, as provided herein, the grating can be moved about a grating pivot axis that is parallel to the beam polarization and perpendicular to the fast axis of the gain medium to adjust the wavelength of the light beam. This orientation allows for mode hop-free operation of the laser assembly. Further, in certain embodiments, one or more of the grating ridges have an approximately rectangular cross-sectional profile. As provided herein, this unique ridge profile enhances the reflectivity of the grating to a beam polarization that is parallel to the grating ridges.

In one embodiment, the gain medium is a laser diode. Alternatively, the gain medium can be an Interband Cascade gain medium. Further, in certain embodiments, the light beam emitting from the gain medium has a center wavelength of approximately 3.2 microns.

Additionally, in certain embodiments, the laser assembly includes a grating mover that moves the diffraction grating relative to the gain medium about the grating pivot axis to tune the lasing frequency of the external cavity. In this embodiment, the grating mover can sequentially move the diffraction grating so that the light beam continuously tunes over different center wavelengths.

Moreover, the laser assembly can include (i) an output coupler which reflects at least of a portion of the light back to the gain medium, the output coupler cooperates with the grating to form the external cavity; (ii) a cavity collimator positioned between the gain medium and the diffraction grating, the cavity collimator having a collimator apex located on a collimator surface that faces the grating; wherein light exiting the collimator is collimated and travels along an optical axis, and wherein light between the collimator apex and the output coupler travels an apex/coupler group optical length which is equal to the effective distance that a ray of light propagates during movement from the collimator apex to the output coupler; and (iii) a beam attacher that retains the grating and allows the grating to effectively pivot about a grating pivot axis that is located approximately in a pivot plane, the grating pivot plane being normal to the optical axis, the grating pivot plane being spaced apart from the collimator apex a distance along the optical axis that is equal to the apex/coupler group optical length.

The present invention is also directed to an imaging system and method for imaging an emitting gas. In this embodiment, the imaging system can include an infrared camera that captures an image of light in the mid-infrared range, and the laser assembly provided herein generating the laser beam directed at the emitting gas. It should be noted that the laser assembly provided herein can be used in applications other than gas imaging.

Additionally, the present invention is directed to a method for generating a light beam, the method comprising the steps of: (i) directing electrical current through a gain medium that emits from both facets, wherein a beam polarization of the light beam emitting from the second facet is perpendicular to the growth direction and the fast axis; and (ii) positioning a diffraction grating in the path of the laser beam that emits from the second facet, the grating including a plurality of grating grooves that are oriented substantially parallel to the beam polarization.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1:
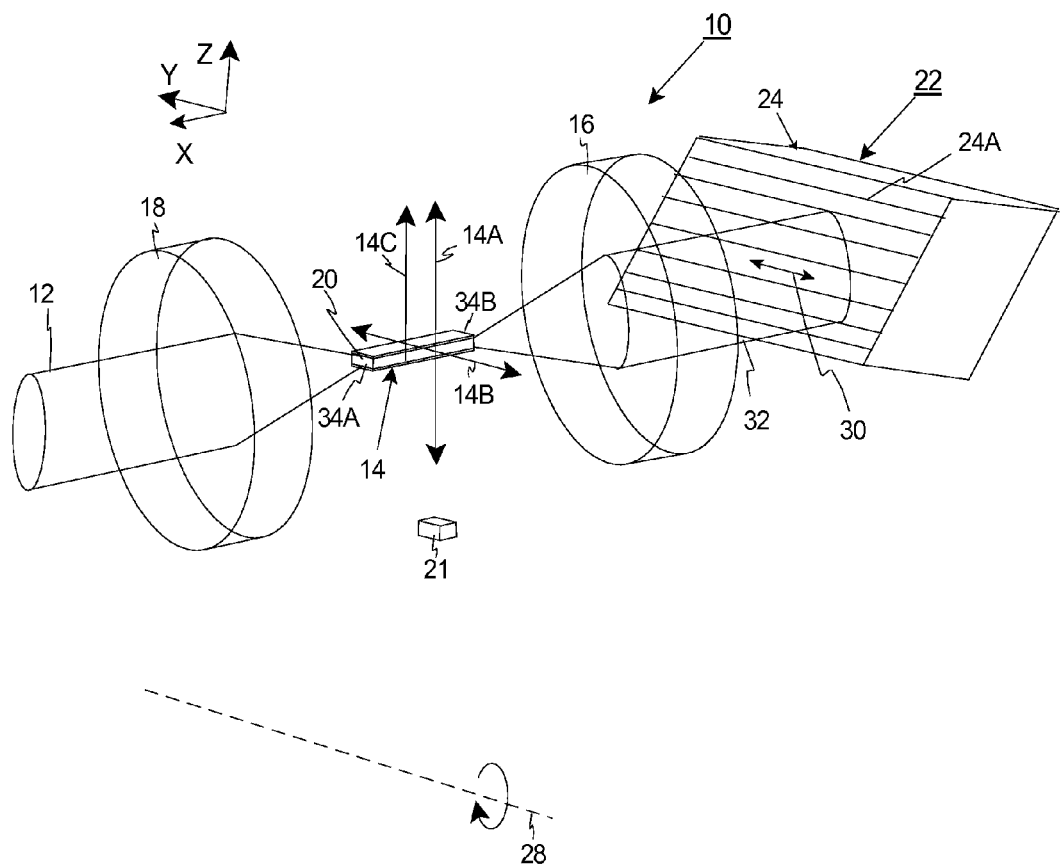
FIG. 1 is a simplified illustration of a laser assembly having features of the present invention.

FIG. 1 is a simplified illustration of a laser assembly 10 that can be used to selectively generate a mode hop-free, continuously wavelength tunable output light 12 over a wavelength range supported by a gain medium 14 of the laser assembly 10. In FIG. 1, the laser assembly 10 includes the gain medium 14, a cavity collimator 16, an output collimator 18, an output coupler 20, a control system 21 (illustrated as a box), and a wavelength dependent ("WD") feedback assembly 22 that cooperate to generate the wavelength selectable, output light 12. In certain embodiments, the WD feedback assembly 22 includes a diffraction grating 24 that cooperates with the output coupler 20 to define an external cavity of the laser assembly 10. Further, the WD feedback assembly 22 can include a feedback mover 426 (illustrated in FIG. 4) that moves and pivots the grating 24 about a grating pivot axis 28. It should be noted that the approximate location of the grating pivot axis 28 is illustrated in FIG. 1. A more complete discussion of the location of the grating pivot axis 28 is described below and illustrated in FIG. 4.

As an overview, the grating 24 including a plurality of grating ridges 24A (Illustrated as lines in FIG. 1) that are oriented parallel to a beam polarization 30 (illustrated of an arrow) of an intracavity beam 32 that is incident on the grating 24. With this design, the grating 24 can be moved about a grating pivot axis 28 that is parallel to the beam polarization 30 and perpendicular to a fast axis 14A of the gain medium 14 to selectively adjust the wavelength of the output light beam 12. This orientation allows for mode hop-free operation of the laser assembly 10. Further, in certain embodiments, one or more of the grating ridges 24A have an approximately rectangular shaped cross-sectional profile. As provided herein, this unique profile of the ridges 24A enhances the reflectivity of the grating 24 to a beam polarization 30 that is parallel to the grating ridges 24A.

In certain embodiments, the laser assembly 10 generates the output light beam 12 that is in the mid-infrared ("MIR") range. In one embodiment, as used herein, the MIR range is approximately 2-20 microns. In addition, the laser assembly 10 can be controlled to generate the output beam 12 having any desired wavelength characterized by linewidths of 1-30 MHz within the output wavelength range, and also can be controlled to continuously change the wavelength within the output wavelength range. Furthermore, the laser assembly 10 can be designed to generate an output beam 12 that includes an arbitrary set of sequential, specific pulses of light that span the output range. In certain embodiments, the wavelength range is near approximately 3.2 microns. Wavelengths of approximately 3.2 microns are particularly useful in absorption spectroscopy applications since many gases of interest have their fundamental vibrational modes at this wavelength in the MIR range and thus present strong, unique absorption signatures.

Figure 2:
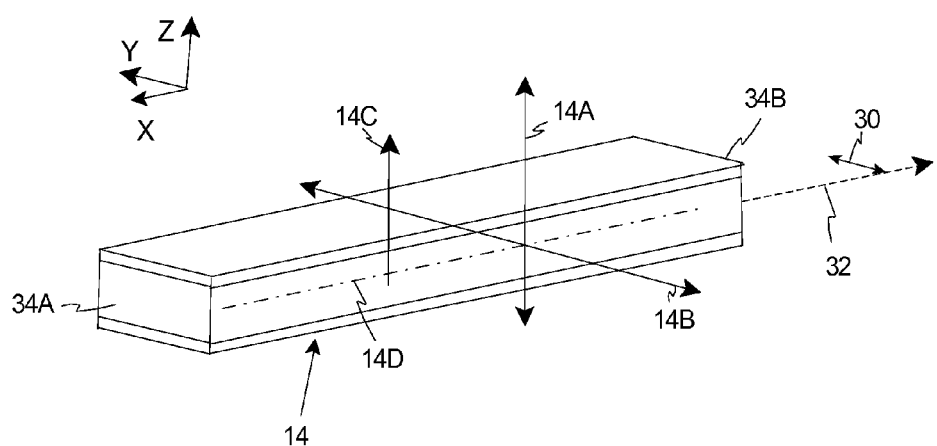
FIG. 2 is a simplified illustration of a portion of the laser assembly of FIG. 1.

Referring to FIGS. 1 and 2, in one embodiment, the gain medium 14 includes (i) a first facet 34A that faces the output collimator 18 and (ii) a second facet 34B that faces the cavity collimator 16 and the grating 24. In this embodiment, the gain medium 14 emits from both facets 34A, 34B.

In one embodiment, the second facet 34B is coated with an anti-reflection ("AR") coating and the first facet 34A is left uncoated or coated with a reflective coating. The AR coating removes coupled cavity effects which interfere with the wavelength selecting ability of the diffraction grating 24. Undesirable residual reflection off the second facet 34B interferes with feedback from the diffraction grating 24 and, if sufficiently large, will defeat the ability of the grating 24 to select one desired laser mode in the course of tuning. In contrast, a reflective coating on the first facet 34A reflects at least some of the light that is directed at the first facet 34A from the gain medium 14 back into the gain medium 14. In this embodiment, the reflective coating acts as the output coupler 20 for the external cavity. Thus, in this embodiment, the output coupler 20 is positioned directly against the gain medium 14. Alternatively, a separate reflector (not shown) can be positioned between the gain medium 14 and the output collimator 18 to function as the output coupler 20.

In one non-exclusive embodiment, the AR coating can have a reflectivity of less than 1% percent, and the reflective coating can have a reflectivity of between approximately 5-95 percent. In certain embodiments, it is preferred that the AR coating can provide the lowest possible reflection off the second facet 34B across the complete tuning range.

In one embodiment, the gain medium 14 is a type I Laser Diode. Alternatively, the gain medium 14 can be an Interband Cascade Lasers (ICL). When the gain medium 14 is a type I Laser Diode or an ICL, the polarization 30 of the light 32 that exits the second facet 34B is (i) aligned with and parallel to a slow axis 14B of the gain medium 14 and (ii) perpendicular to the fast axis 14A of the gain medium 14. In this embodiment, (i) the fast axis 14A is aligned with a growth direction 14C (represented by an arrow and aligned with the Z axis in this example) of the gain medium 14, (ii) the fast axis 14A is aligned with the narrow dimension (along the Z axis) of the gain medium 14, and (iii) the slow axis 14B is aligned with the wide dimension (along the Y axis) of the gain medium 14. Stated in another fashion, for a type I Laser Diode or an ICL gain medium 14, the beam polarization 30 is S polarization (into the page along the Y axis), and is perpendicular to the growth direction 14C of the gain medium 14.

Further, in certain embodiments, the gain medium 14 operates as a single transverse mode waveguide. Thus, light in the gain medium 14 moves along a medium longitudinal axis 14D of the gain medium 14.

As provided herein, the grating 24 has a grating pivot axis 28 that is oriented perpendicular to the fast axis 14A of the gain medium 14 in order to minimize the possibility of multimode behavior or mode hops. In this embodiment, the grating pivot axis 28 is parallel to the Y axis and the beam polarization 30.

The cavity collimator 16 is positioned between the gain medium 14 and the grating 24, and collimates and focuses the light that passes between these components. For example, the cavity collimator 16 can include one or more cavity lenses. For example, the cavity lens can be a single meniscus, aspherical, lens that has an optical axis. In one embodiment, to achieve the desired small size and portability, the cavity lens has a relatively small diameter. The cavity lens can be made of an IR transparent material that is selected from the group of Ge, ZnSe, ZnS Si, CaF, BaF, or chalcogenide glass. However, other materials may also be utilized. The cavity lens can be designed to have a relatively large numerical aperture (NA). For example, the cavity lens can have a numerical aperture of at least approximately 0.6-0.9.

Moreover, the cavity lens can be designed to have (i) diffraction limited collimation across the full numerical aperture, (ii) aplanatic performance, (iii) low dispersion or dispersion compensation over the tunable range, and/or (iv) desired beam size upon collimation, to efficiently illuminate the diffraction grating 24 for highest efficiency and spectral resolving power. Additionally, one or both sides of the cavity lens can be coated with a spectrally broadband, high efficiency AR coating.

The output collimator 18 is spaced apart from the first facet 34A of the gain medium 14, and the output collimator 18 collimates the light 12 that exits the first facet 34A of the gain medium 14. For example, the output collimator 18 can include one or more lens that is somewhat similar in design to the cavity lens described above.

The control system 21 includes a processor and is used to selectively direct power to the gain medium 14, and to control the grating mover 426.

The wavelength dependent ("WD") feedback assembly 22 includes the grating 24 that reflects the light back to the cavity lens 16 and the gain medium 14; and the grating 24 is used to precisely adjust the lasing frequency of the external cavity and the wavelength of the output light 12. Stated in another fashion, the grating 24 is used to feedback to the gain medium 14 a relatively narrow band wavelength which is then amplified in the gain medium 14. In one embodiment, the diffraction grating 24 has wavelength-dependent reflectivity, and the diffraction grating 24 cooperates with the output coupler 20 to form the external cavity. With this design, the output light 12 can be tuned and set to a desired fixed wavelength with the grating 24 without adjusting the gain medium 14. Thus, in the external cavity arrangements disclosed herein, the grating 24 dictates what laser mode will experience the most gain and thus define the wavelength of the output light 12. With this design, the precise movement of the diffraction grating 24 relative to the cavity collimator 16 and the gain medium 14 adjusts the lasing wavelength and the wavelength of the output light 12 without mode hops.

In alternative, non-exclusive embodiments, the grating 24 can be used to control the wavelength of output light 12 within the output wavelength range to within approximately 0.0003 nanometers. In certain embodiments, with the designs provided herein, the output light 12 has a narrow linewidth. In non-exclusive examples, the laser source 10 can be designed so that the linewidth of the output light 12 is less than approximately 0.001 nm. The spectral width of the output light 12 can be adjusted by adjusting the cavity parameters of the external cavity and stability of laser electrical current, temperature control and mechanical rigidity of the external cavity.

Figure 3A:
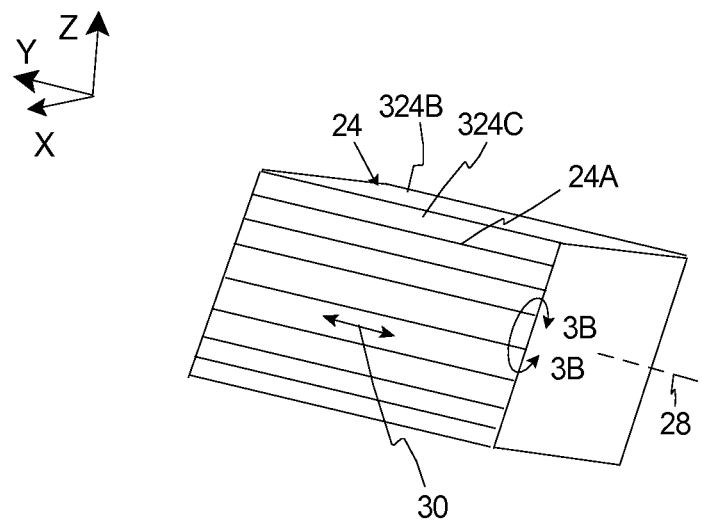
FIG. 3A is a simplified illustration of another portion of the laser assembly of FIG. 1.
Figure 3B:
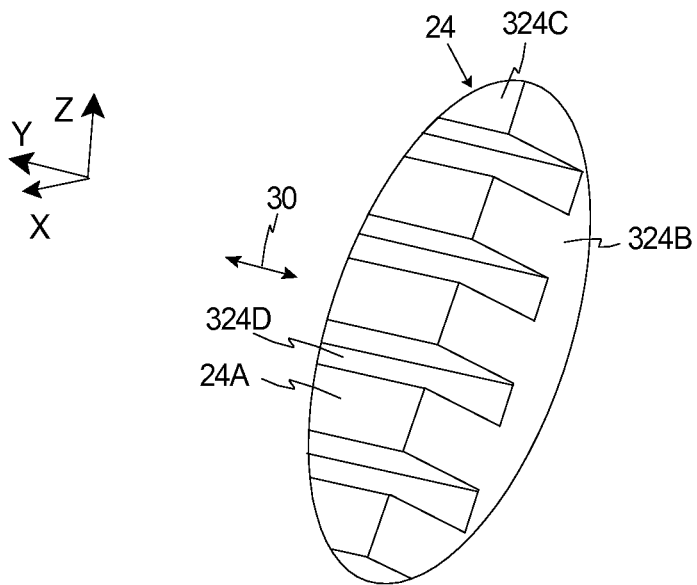
FIG. 3B is an enlarged illustration taken from FIG. 3A.

FIG. 3A is a perspective view of one embodiment of the diffraction grating 24 and FIG. 3B is an enlarged view of a portion of the diffraction grating 24 of FIG. 3A. In this embodiment, the diffraction grating 24 is a reflective grating that includes a generally rectangular shaped grating body 324B having a grating face surface 324C that contains an array of spaced apart grating ridges 24A that are defined by spaced apart grating grooves 324D. Stated in another fashion, the diffraction grating 24 includes a glass or polished metal grating face surface 324C having a large number of very fine parallel grooves 324D that have a grating period ("GP"). With this design, movement of the grating face surface 324B relative to the gain medium 14 (illustrated in FIG. 1) and the incident beam 32 (illustrated in FIG. 1) changes the angle of incidence of the incident beam 32 onto the grating face surface 324B and the wavelength of the light in the external cavity.

In this embodiment, each of the grating ridges 24A has a generally rectangular shaped cross-sectional profile, and each ridge 24A is defined by a pair of spaced apart, generally rectangular shaped grating grooves 324D. As provided herein, the generally rectangular shaped ridges 24A and grooves 324D (a "right angle" profile) will provide high reflectivity and high bandwidth for light that is polarized parallel to the grating grooves 324D. In this embodiment, the grating ridges 24A and the grating grooves 324D are aligned with and parallel to the S polarization 30 of the beam 32 along the Y axis. The high efficiency and high bandwidth of this grating 24 with respect to light polarized parallel to the grooves 324D of the grating 24 allow for the grating pivot axis 28 to remain perpendicular to the fast axis 14A (illustrated in FIG. 1) of the gain medium 14 (illustrated in FIG. 1). Thus, the wobble in the light induced by the rotation of the grating 14 will not induce mode hops or multimode behavior in the light beam 12 (illustrated in FIG. 1).

Stated in another fashion, with this design, the grating 24 can be moved about a grating pivot axis 28 that is parallel to the beam polarization 30 and perpendicular to the fast axis 14A of the gain medium 14 to adjust the wavelength of the light beam 12. This orientation allows for mode hop-free operation of the laser assembly 10. The reason this orientation is optimum is because as the grating 24 rotates, it can cause a small amount of wobble in the light beam 12 as it returns to the cavity collimator 18. This wobble will be in an angular direction perpendicular to the grating pivot axis 28. The fast axis 14A of the gain medium 14 is much less susceptible to misalignment of the cavity due to this wobble than the slow axis 14B of the gain medium 14. Therefore if the wobble due to rotation of the grating 24 is in the direction of the fast axis 14A of the gain medium 14, then the cavity will be much more robust to multimode behavior and mode hops.

Desirable features of the diffraction grating 24 include (i) highest reflection efficiency in working order across broadest spectral range, (ii) diffraction limited flatness across working area, and/or (iii) a physical size which guarantees that no portion of collimated light from the cavity collimator 16 (illustrated in FIG. 1) will miss the working area as the grating 24 is moved in a manner prescribed in the present invention.

Alternatively, the grating 24 can have a different configuration than that illustrated in FIGS. 3A and 3B.

As provided herein, if a typical diffraction grating having substantially triangular shaped grooves and ridges was utilized, it will provide low (possibly insufficient) reflection efficiency for a beam having a polarization that is parallel to the grating grooves.

Additionally, in contrast, if the assembly 10 was designed so that the grating pivot axis is parallel to the fast axis of the gain medium in order to take advantage of the high reflectivity and bandwidth of a triangular groove profile of a traditional grating, beam wobble can be induced by the grating rotation being parallel to the slow axis of the gain medium. In this case, the beam wobble could induce mode hops or multimode behavior in the light beam due to the wider acceptance angle of the gain medium 14 in the direction of the slow axis. To achieve mode hop-free ("MHF") operation, there is a need to maintain the grating rotation axis orientation to maintain high reflectivity and high bandwidth of the grating 24.

Figure 4:
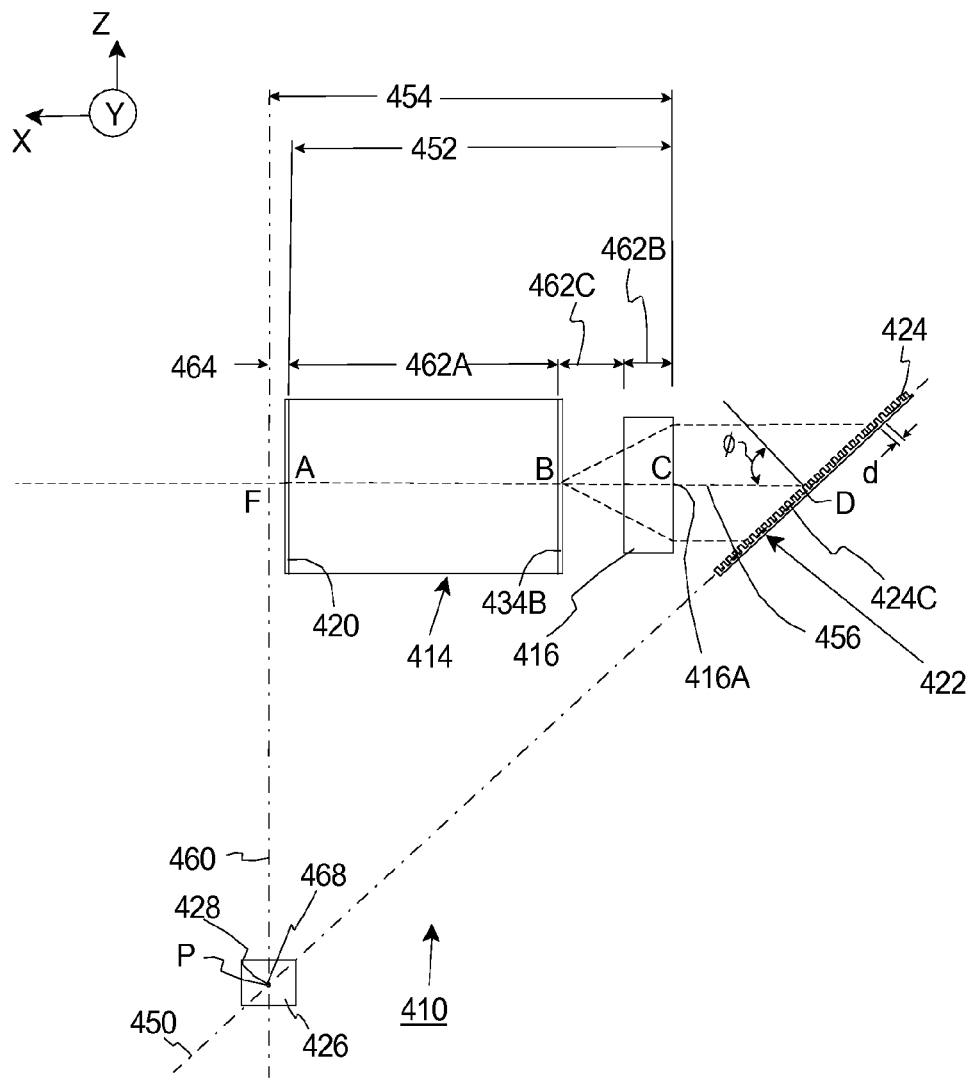
FIG. 4 is a simplified illustration of another embodiment of a laser assembly having features of the present invention.

FIG. 4 is a simplified illustration of a laser assembly 410 that can be used to selectively generate a mode hop-free, continuously wavelength-tunable output light 12 (illustrated in FIG. 1) over the wavelength range supported by the a gain medium 414. The simplified illustration of the laser assembly 410 in FIG. 4 only illustrates the gain medium 414, the cavity collimator 416, the output coupler 420, and the wavelength dependent feedback assembly 422 that are similar to the corresponding components described above and illustrated in FIG. 1.

In this embodiment, the feedback assembly 422 includes the diffraction grating 424 having the grating face surface 424C that is in a grating plane 450, and the grating mover 426. As provided herein, a unique grating pivot axis 428 (into the page along the Y axis in the example illustrated in FIG. 4) exists about which the diffraction grating 424 can be pivoted to move the diffraction grating 424 relative to the gain medium 414 to continuously adjust the wavelength of the output light 12 over a certain range. As a result thereof, the laser source 410 can produce a mode hop free, continuously wavelength tunable output light 12.

In this embodiment, the cavity collimator 416 includes a collimator apex 416A located on the lens surface that faces the grating 424. With the present design, light traveling between the collimator apex 416A and the output coupler 420 travels an apex/coupler physical length 452 and an effective apex/coupler group optical length 454, and light exiting the cavity collimator 416 at the collimator apex 416A towards the grating 424 travels along an optical axis 456.

As provided herein, the unique grating pivot axis 428 is located approximately at an intersection of the grating plane 450 and a pivot plane 460. Further, as provided herein, the pivot plane 460 is normal to the optical axis 456. Moreover, the pivot plane 460 is spaced apart from the collimator apex 416A a distance that is equal to the apex/coupler group optical length 454. Stated in another fashion, any ray that travels from the collimator apex 416A, through the gain medium 414 and hits the output coupler 420, then the optical distance this ray traveled is the number we are trying to determine to locate the pivot axis 428. The calculation of the apex/coupler group optical length 454 is described in more detail below.

In one non-exclusive embodiment, the gain medium 414 has a medium length 462A along the medium axis (along the X axis in FIG. 4) of approximately 3 millimeters. Alternatively, the gain medium 414 can have a medium length 462A of between approximately 0.5 to 5 millimeters. Additionally, the gain medium 414 has an index of refraction that is different than the index of refraction for air. In alternative, non-exclusive examples, the gain medium 414 can have an index of refraction of approximately 3 to 3.5.

Additionally, the cavity lens 416 has an index of refraction that is different than the index of refraction for air. In alternative, non-exclusive examples, the cavity lens 416 can have an index of refraction of approximately 2.5 (for Zinc Selenium "ZnSe"), 3.4 (for Silicon "Si"), 4.01 (for Germanium "Ge"), or 3.3 (for Gallium Arsenic "GaAs"). Moreover, the cavity lens 416 has a lens thickness 462B along the axis of the lens. For example, the lens thickness 462B can be between approximately 0.5 to 4 millimeters. In one, non-exclusive embodiment, the lens thickness 462B is approximately 2.2 millimeters.

FIG. 4 is useful for illustrating how to determine (i) the location of the pivot plane 460, and (ii) the location of the grating pivot axis 428 (also represented a P). During operation of the laser source 410, a plurality of light rays travel between the gain medium 414, the cavity collimator 416 and the grating 424. In FIG. 4, the travel of a ray in the external cavity is highlighted with the letters A, B, C, D. More specifically, (i) D represents the point where the ray is incident on or reflected off of the grating 424, (ii) C represents the point where the ray exits the cavity collimator 416 towards the grating 424 or enters the cavity collimator 416 (at the collimator apex 416A) from the grating 414, (iii) B represents the point wherein the ray exits or enters the second facet 434B of the gain medium 414, and (iv) A represents the point where the ray is incident on or reflects off of the output coupler 420.

In this example, the ray segment CD is on the optical axis 456, ray segment AB represents the single transversal mode of the light in the gain medium 414, and ray segment B-C-D is an arbitrary ray emerging from the gain medium 414. Further, in FIG. 4, dashed line DF represents an imaginary straight line that is coaxial with and passes through the optical axis 456. Moreover, in FIG. 4, PD represents the grating plane 450. Additionally, in FIG. 4, the grating period is also represented by the letter d. Further, the optical axis 456 is at an angle of $\phi$ relative to normal to the grating plane 450.

As provided herein, in one embodiment, the pivot plane 460 is normal to the optical axis 456, and the pivot plane 460 is located outside the external cavity near and spaced apart from the optical output coupler 420. Further, the pivot plane 460 is spaced apart the apex/coupler group optical length 454 from the collimator apex 416A along the optical axis 456. Stated in another fashion, the pivot plane 460 is spaced apart a separation distance 464 from the output coupler 420 and the separation distance 464 is equal to the apex/coupler group optical length 454 minus an apex/coupler physical length 452. In FIG. 4, the letter F represents the intersection between the pivot plane 460 and the optical axis 456.

As provided above, the term apex/coupler group optical length 454 shall mean the effective distance that any ray of light travels during movement in the external cavity from the collimator apex 416A to the output coupler 420. More specifically, the apex/coupler group optical length 454 takes in account the index of refraction of all objects in the external cavity that influence the movement of a ray in the external cavity. As provided herein, the apex/coupler group optical length 454 is longer than the apex/coupler physical length 452 because the index of refraction of the gain medium 414 and the cavity collimator 416 is less than one. The apex/coupler group optical length 454 can be expressed as follows in Equation 1:

$$L\_opt = \Sigma n_i L_i$$

Where L_opt is the apex/coupler group optical length 454, i is each portion of the external cavity, n is the group index of refraction of each portion of the external cavity, and L is the length of each portion of the external cavity.

In FIG. 4, the apex/coupler group optical length 454 is the effective length that a particular ray travels in the external cavity between the collimator apex 416A and the output coupler 420 and is equal to the apex/coupler physical length 452 multiplied by the index of refraction in which the ray travels. If there are multiple different objects in the external cavity, then the apex/coupler group optical length 454 is the sum of each element length multiplied by its group index of refraction. For example, in FIG. 4, the apex/coupler group optical length 454 is the sum of (i) the medium length 462A multiplied by the group index of refraction of the gain medium 414, (ii) a fluid space length 462C multiplied by the group index of refraction of the fluid, and (iii) the lens thickness 462B multiplied by the group index of refraction of the cavity lens 416. It should be noted, that in this embodiment, because the ray travels in air between the collimator apex 416A and the grating 424, the physical and optical length are the same for this area. In this example, the apex/coupler group optical length 454 can be expressed as follows in Equation 2:

$$L\_opt = (L\_\text{gain medium} \cdot n\_\text{gain medium}) + (L\_\text{1fluid space} \cdot n\_\text{fluid}) + (L\_\text{optical lens} \cdot n\_\text{collimator}).$$

In Equation 2, L is length, and n is the group index of refraction. For air, the index of refraction is 1. Thus, for the laser source 410 illustrated in FIG. 4, the group index of refraction of the gain medium (n_gain medium) and the group index of refraction of the cavity collimator 416 (n_collimator) influence the rays that travel in the external cavity and the location of the resulting pivot axis 4. Further, as provided herein, the apex/coupler group optical length 454 is the distance between F and C in FIG. 4.

As used herein, the term apex/coupler physical length 452 shall mean the actual physical length that any ray of light travels during movement in the external cavity from the output coupler 420 to the collimator apex 416A (Path ABC in FIG. 4). For example, in the embodiment illustrated in FIG. 4, the apex/coupler length 452 is the length that a particular ray travels and is the sum of (i) the medium length 462A, (ii) the fluid space length 462C, and (iii) the lens thickness 462B.

Basically, the apex/coupler physical length 452 can be calculated similar to the apex/coupler group optical length 454 except the index of refraction for each segment is assumed to be equal to 1. Thus, in this example, the apex/coupler physical length 452 can be expressed as follows in Equation 5:

$$L\_phy = \Sigma(L\_\text{gain medium} \cdot 1) + (L\_\text{1fluid space} \cdot 1) + (L\_\text{optical lens} \cdot 1)$$

Or $$L\_phy = \Sigma(L\_\text{gain medium}) + (L\_\text{1fluid space}) + (L\_\text{optical lens}).$$

It should be noted that the apex/coupler group optical length 454 is always greater than the apex/coupler physical length 452 by the separation distance 464.

In one simplified example, if the gain medium 414 has a medium length 462A of 3 millimeters and a substantially constant index of refraction of 3.3 over the desired wavelengths, and the cavity collimator 416 has a lens thickness 462B of 2.2 millimeters and a substantially constant index of refraction of 4.1, then the separation distance 464 can be calculated as follows:

$$\begin{aligned}
\Delta &= L\_opt - L\_phy \\
&= (L\_\text{gain medium} \cdot (n\_\text{gain medium} - 1)) + \\
&\quad (L\_\text{optical lens} \cdot (n\_\text{collimator} - 1)) \\
&= (3 \cdot (3.3 - 1)) + (2.2 \cdot (4.1 - 1)) \\
&= 13.72 \text{ millimeters}
\end{aligned}$$

In this example, the pivot plane 50 is spaced apart from the output coupler 420 by a distance of 13.72 millimeters along the optical axis 456.

It should be noted that in the embodiment of the laser assembly 410 illustrated in FIG. 4, the optical axis 456, the cavity collimator 416, and the gain medium 614 are all aligned along the X axis and these axes are coaxial.

In this embodiment, the feedback assembly 422 includes a rigid grating beam (not shown), a beam attacher 468, and the grating mover 426 that cooperate to retain the diffraction grating 424 and precisely move and position the diffraction grating 424 about the grating pivot axis 428.

In one embodiment, the beam attacher 468 secures the proximal beam end of the grating beam to a mounting base (not shown) and allows the grating beam and the grating 424 to effectively pivot relative to the mounting base about the pivot axis 428. For example, the beam attacher 468 can include a pin (not shown) that is fixedly secured to the mounting base and an attacher bearing (not shown) that pivotable attaches the grating beam to the mounting base. Further, in this embodiment, the attacher bearing is positioned on and pivots about the pivot axis 428.

The grating mover 426 moves the grating beam so that the grating 424 effectively rotates about the pivot axis 428. For example, the grating mover 426 can include an electric actuator that precisely rotates the grating beam 466 about the pivot axis 428. With this design, the control system 21 (illustrated in FIG. 1) can be used to precisely control the grating mover 426 to precisely select the desired wavelength of the output light 12 generated by the laser assembly 410.

An additional discussion of the location of the grating pivot axis is contained in U.S. Pat. No. 7,733,925 that issued on Jun. 8, 2010, and entitled "CONTINUOUS WAVELENGTH TUNABLE LASER SOURCE WITH OPTIMUM POSITIONING OF PIVOT AXIS FOR GRATING". As far as permitted, the contents of U.S. Pat. No. 7,733,925 are incorporated herein by reference.

Figure 5:
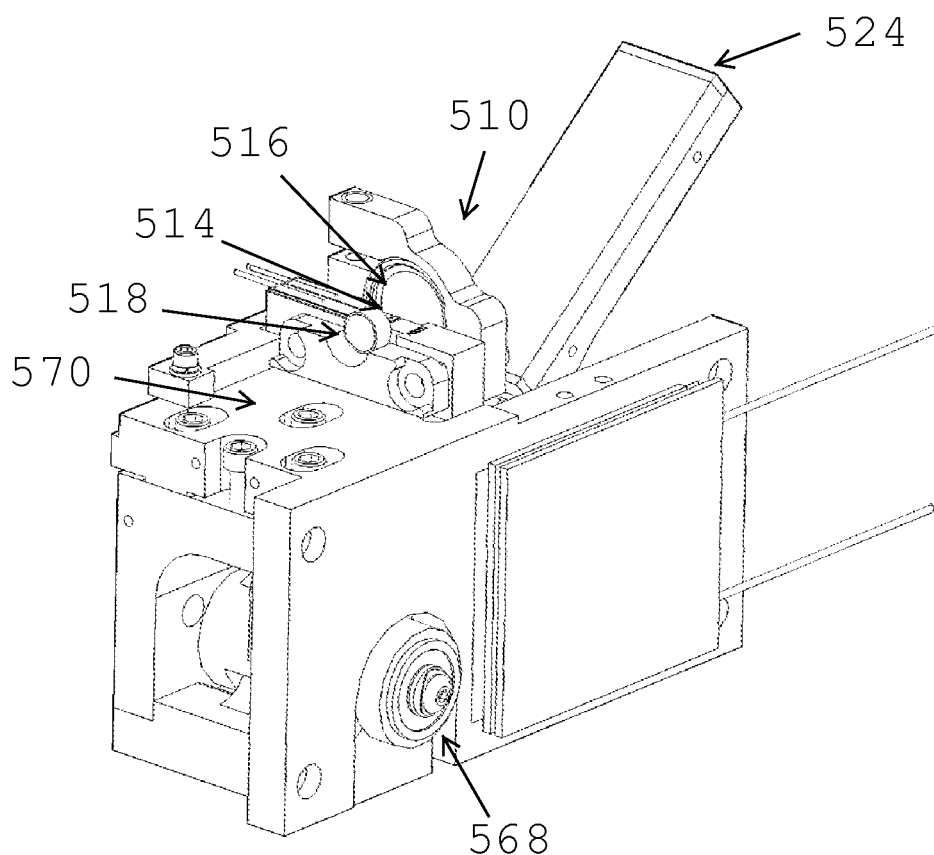
FIG. 5 is a perspective view of still another embodiment of a laser assembly having features of the present invention.

FIG. 5 is a simplified illustration of an implementation of the laser assembly 510 that includes the gain medium 514, the cavity collimator 516, the output collimator 518, and an assembly frame 570. FIG. 5 also illustrates the beam attacher 568 of the grating 524.

Figure 6A:
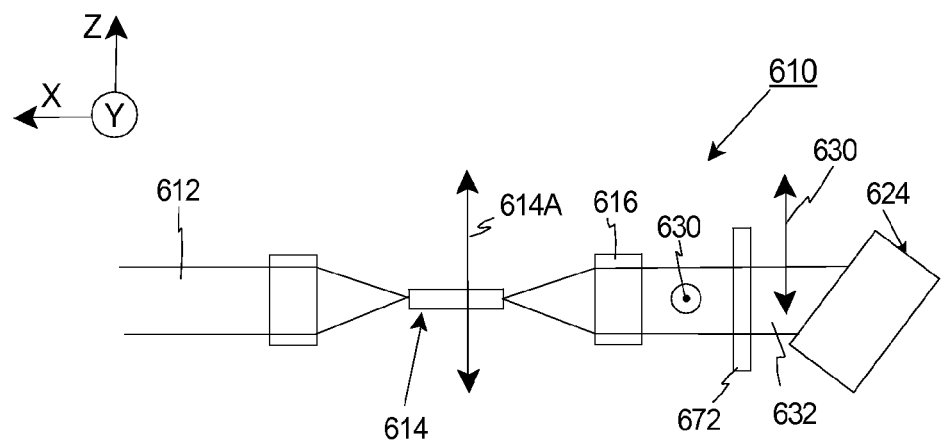
FIG. 6A is a simplified side illustration of yet another embodiment of a laser assembly having features of the present invention.

FIG. 6A is a simplified side illustration of yet another embodiment of a laser assembly 610 that is somewhat similar to the laser assembly 10 described above and illustrated in FIG. 1. However, in this embodiment, the laser assembly 610 includes a halfwave plate 672 positioned between the cavity collimator 616 and the grating 624. In this embodiment, for rays traveling from the gain medium 614 (from left to right in FIG. 6A) through the halfwave plate 672, the halfwave plate 672 rotates the beam polarization 630 (illustrated with a circle) of the cavity beam 632 from s-polarization (perpendicular to fast axis 614A and growth direction) to a p-polarization 630 (parallel to fast axis 614A and growth direction). Further, for rays traveling from the grating 624 (from right to left in FIG. 6A) through the halfwave plate 672, the halfwave plate 672 rotates the beam polarization 630 of the cavity beam 632 from p-polarization to s-polarization.

Figure 6B:
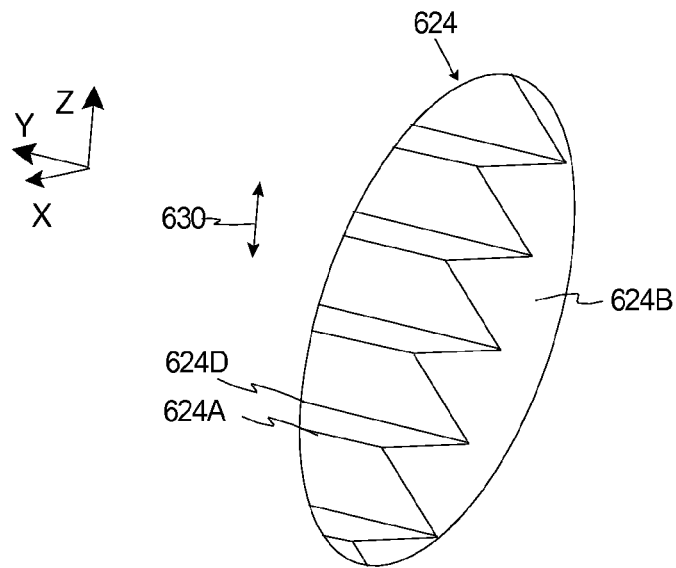
FIG. 6B is an enlarged view of a portion of the laser assembly of FIG. 6A.

FIG. 6B is an enlarged view of a portion of the diffraction grating 624 of FIG. 6A. In this embodiment, the diffraction grating 624 is a reflective grating that includes a generally rectangular shaped grating body 624B having a grating face surface that contains an array of spaced apart grating ridges 624A that are defined by spaced apart grating grooves 624D. In this embodiment, each of the grating ridges 624A has a generally triangular shaped cross-sectional profile, and each ridge 624A is defined by a pair of spaced apart, generally triangular shaped grating grooves 624D. This design will provide high reflectivity and high bandwidth for light that is polarized perpendicular to the grating grooves 624D. In this embodiment, the grating ridges 624A and the grating grooves 624D are perpendicular with the P polarization 630 after the half waveplate 672.

The high efficiency and high bandwidth of the grating 624 with respect to light polarized perpendicular to the grooves 624D allow for the grating pivot axis 628 (illustrated with a circle) to be perpendicular to the fast axis 614A. Thus, the wobble in the light induced by the rotation of the grating 614 will not induce mode hops or multimode behavior in the light beam 612 (illustrated in FIG. 1).

Referring back to FIG. 6A, in this embodiment, the halfwave plate 672 would have the effect of rotating the polarization 630 of the light beam 632 but not the direction of the wobble of the light beam 632 induced by the grating 624 rotation. With this design, the grating 624 can be moved about a grating pivot axis 628 that is perpendicular to the beam polarization and perpendicular to the fast axis 614A.

This embodiment requires the insertion of the additional waveplate 672 and thus requires an extension to the overall cavity. A short cavity length is desired for mode hop-free operation.

Figure 7:
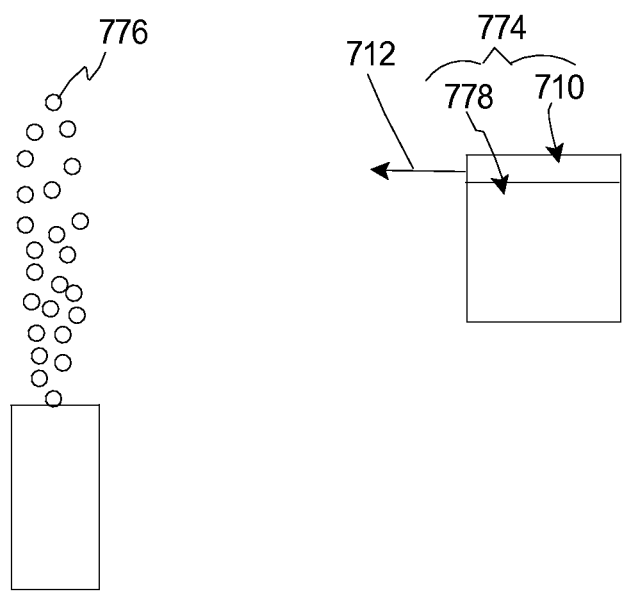
FIG. 7 is a simplified illustration of an imaging system having features of the present invention.

FIG. 7 is simplified illustration of an imaging system 774 for detecting an emitting gas 776. In this embodiment, the imaging system 774 includes (i) a laser source 710 that illuminates the area near the emitting gas 776, and (ii) an imager 778 (i.e. an infrared camera) that captures real-time, high resolution thermal images of the emitting gas 776 that can be displayed or recorded for future viewing. As non-exclusive examples, the imaging system 774 is useful for locating emitting gas 776 (i.e. leaks) in the oil, gas, utility, chemical industries, as well as locating emitting gas 776 for homeland security.

The laser source 710 can be similar in design to the laser sources 10 described above. For example, the laser source 710 can rapidly and accurately generate one or more sets of sequential, wavelength specific output pulses 712 that span a predetermined detection range (e.g. the mid-infrared range).

The imager 778 captures the thermal image of the emitting gas 776 and the surrounding environment. In one embodiment, the imager 778 is an infrared camera that provides real-time, high resolution thermal images of the emitting gas 776 that can be displayed on a display or recorded for future viewing.

While the particular designs as shown and disclosed herein is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An external cavity laser assembly for generating a light beam, the laser assembly comprising:
   a gain medium having a growth direction, a fast axis, a first facet, and a second facet that is spaced apart from the first facet, the gain medium generating the light beam when electrical current is directed through gain medium, the gain medium emitting from both facets, wherein a beam polarization of the light beam emitting from the second facet is perpendicular to the growth direction and the fast axis; and
   a diffraction grating positioned in the path of the laser beam that emits from the second facet, the grating including a plurality of grating ridges that are oriented substantially parallel to the beam polarization.

2. The laser assembly of claim 1 wherein the gain medium is a laser diode.

3. The laser assembly of claim 1 wherein the gain medium is an Interband Cascade gain medium.

4. The laser assembly of claim 1 further comprising a grating mover that moves the diffraction grating relative to the gain medium about a grating pivot axis to tune the lasing frequency of the external cavity, wherein the grating pivot axis is approximately parallel to the beam polarization.

5. The laser assembly of claim 4 wherein the grating mover moves the diffraction grating so that the light beam continuously tunes to different center wavelengths.

6. The laser assembly of claim 1 further comprising a half waveplate positioned between the gain medium and the grating, and wherein at least one of the grating ridges has a substantially triangular shaped cross-sectional profile.

7. The laser assembly of claim 1 wherein at least one of the grating ridges has a substantially rectangular shaped cross-sectional profile.

8. The laser assembly of claim 1 further comprising (i) an output coupler which reflects at least of a portion of the light back to the gain medium, the output coupler cooperating with the grating to form the external cavity; (ii) a cavity collimator positioned between the gain medium and the diffraction grating, the cavity collimator having a collimator apex located on a collimator surface that faces the grating; wherein light exiting the collimator is collimated and travels along an optical axis, and wherein light between the collimator apex and the output coupler travels an apex/coupler group optical length which is equal to the effective distance that a ray of light propagates during movement from the collimator apex to the optical output coupler; and (iii) a beam attacher that retains the grating and allows the grating to effectively pivot about a grating pivot axis that is located approximately in a pivot plane, the pivot plane being normal to the optical axis, the pivot plane being spaced apart from the collimator apex a distance along the optical axis that is equal to the apex/coupler group optical length.

9. An imaging system for imaging an emitting gas, the imaging system comprising an imager that is adapted to capture an image of light in the mid-infrared range, and the laser assembly of claim 1 generating the laser beam directed at the emitting gas.

10. An external cavity laser assembly for generating a light beam, the laser assembly comprising:
    a gain medium having a growth direction, a fast axis, a first facet, and a second facet that is spaced apart from the first facet, the gain medium generating the light beam when power is directed to the gain medium, the gain medium emitting from both facets, wherein a beam polarization of the light beam emitting from the second facet is perpendicular to the growth direction and the fast axis;
    a diffraction grating positioned in the path of the laser beam that emits from the second facet, the grating including a plurality of grating ridges that are substantially parallel to the beam polarization, wherein each of the grating ridges has a substantially rectangular shaped cross-sectional profile; and
    a grating mover that moves the diffraction grating relative to the gain medium about a grating pivot axis to tune the lasing frequency of the external cavity, wherein the grating pivot axis is approximately parallel to the beam polarization.

11. The laser assembly of claim 10 wherein the gain medium is a laser diode.

12. The laser assembly of claim 10 wherein the gain medium is an Interband Cascade gain medium.

13. The laser assembly of claim 10 wherein the grating mover moves the diffraction grating so that the light beam includes continuously tunable different center wavelengths.

14. The laser assembly of claim 10 further comprising (i) an output coupler which reflects at least of a portion of the light back to the gain medium, the output coupler cooperating with the grating to form the external cavity; (ii) a cavity collimator positioned between the gain medium and the diffraction grating, the cavity collimator having a collimator apex located on a collimator surface that faces the grating; wherein light exiting the collimator is collimated and travels along an optical axis, and wherein light between the collimator apex and the output coupler travels an apex/coupler group optical length which is equal to the effective distance that a ray of light propagates during movement from the collimator apex to the optical output coupler; and (iii) a beam attacher that retains the grating and allows the grating to effectively pivot about the grating pivot axis, the grating pivot axis being located approximately in a pivot plane, the pivot plane being normal to the optical axis, the pivot plane being spaced apart from the collimator apex a distance along the optical axis that is equal to the apex/coupler group optical length.

15. An imaging system for imaging an emitting gas, the imaging system comprising an imager that is adapted to capture an image of light in the mid-infrared range, and the laser assembly of claim 10 generating the laser beam directed at the emitting gas.

16. A method for generating a light beam, the method comprising the steps of:
    directing power to a gain medium to generate the light beam, the gain medium having a growth direction, a fast axis, a first facet, and a second facet that is spaced apart from the first facet, the gain medium emitting from both facets, wherein a beam polarization of the light beam emitting from the second facet is perpendicular to the growth direction and the fast axis; and
    positioning a diffraction grating in the path of the laser beam that emits from the second facet, the grating including a plurality of grating ridges that are approximately parallel to the beam polarization.

17. The method of claim 16 further comprising the step of moving the grating with a grating mover relative to the gain medium about a grating pivot axis to tune the lasing frequency, wherein the grating pivot axis is approximately parallel to the beam polarization.

18. The method of claim 17 wherein the step of moving includes moving the diffraction grating so that the light beam includes a plurality of sequential pulses of light that have different center wavelengths.

19. The method of claim 16 wherein the step of positioning includes at least one of the grating ridges having a substantially rectangular shaped cross-sectional profile.

20. A method for imaging an emitting gas, the method comprising the steps of (i) generating the laser beam by the method of claim 16, (ii) directing the laser beam at the emitting gas, and (iii) capturing an image of the emitting gas with an infrared camera.

* * * * *